United States Patent
Vig et al.

(10) Patent No.: US 6,260,408 B1
(45) Date of Patent: Jul. 17, 2001

(54) TECHNIQUES FOR SENSING THE PROPERTIES OF FLUIDS WITH A RESONATOR ASSEMBLY

(75) Inventors: John R. Vig, Colts Neck; Arthur Ballato, Oceanport, both of NJ (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/286,093

(22) Filed: Apr. 2, 1999

Related U.S. Application Data (63) Continuation-in-part of application No. 09/078,053, filed on May 13, 1998.

(51) Int. Cl.$^7$ ................................................. G01N 29/00
(52) U.S. Cl. ......................... 73/64.53; 73/54.24; 73/579
(58) Field of Search ...................... 73/54.24, 54.25, 73/54.26, 54.27, 54.41, 61.79, 64.42, 64.53, 579, 580

(56) References Cited

U.S. PATENT DOCUMENTS

| | | | |
|---|---|---|---|
| 2,212,139 | 8/1940 | Baldwin et al. . | |
| 2,536,025 | * 1/1951 | Blackburn | 177/351 |
| 2,743,144 | 4/1956 | Bottom et al. . | |
| 3,572,087 | * 3/1971 | Parks | 73/67.2 |
| 4,399,385 | * 8/1983 | Osaka et al. | 310/328 |
| 5,201,515 | * 4/1993 | Granstaff et al. | 73/54.41 |
| 5,323,638 | * 6/1994 | Langdon | 73/32 A |
| 5,359,541 | * 10/1994 | Pope et al. | 364/497 |
| 5,416,448 | 5/1995 | Wessendorf . | |
| 5,767,407 | * 6/1998 | Sinha | 73/579 |
| 5,852,229 | * 12/1998 | Josse et al. | 73/24.06 |
| 5,869,763 | * 2/1999 | Vig et al. | 73/580 |

OTHER PUBLICATIONS

Hammond et al., "An Acoustic Automotive Engine Oil Quality Sensor", Proceedings of the 1997 IEEE International Frequency Control Symposium, IEEE Catalog No. 97CH36016, pp. 72–80, May 28–30, 1997.

Zhang et al., "Contributions of Amplitude Measurement in QCM Sensors", IEEE Transactions on Ultrasonics, Ferroelectrics, and Frequency Control, vol. 43, No. 5, pp. 942–947, Sep. 1996.

Martin et al., "Measuring Liquid Properties With Smooth— and Textured–Surface Resonators", 1993 IEEE International Frequency Control Symposium, IEEE Catalog No. 0–7903–0905–7/93, pp. 603–608, 1993.

* cited by examiner

*Primary Examiner*—Hezron Williams
*Assistant Examiner*—Charles D. Garber
(74) *Attorney, Agent, or Firm*—Michael Zelenka; George B. Tereschuk (57) ABSTRACT

Techniques for determining the properties of a liquid include placing one or more acoustic crystal resonators in contact with the fluid. An oscillator circuit drives each of the resonators at one or more different modes. A frequency counter connected to the oscillator monitors the operating frequencies of the resonators before and after the surfaces are placed in contact with the liquid. A computer, which is responsive to the outputs of the frequency counter, includes a liquid property system for determining difference frequencies by comparing the operating frequencies measured by the frequency counter with predetermined reference frequencies. The computer calculates the properties of the liquid from the difference frequencies.

8 Claims, 4 Drawing Sheets

TECHNIQUES FOR SENSING THE PROPERTIES OF FLUIDS WITH A RESONATOR ASSEMBLY

CONTINUATION-IN-PART

This application is a Continuation-In-Part of U.S. Patent And Trademark Office application Ser. No. 09/078,053, entitled, "Techniques For Sensing The Properties Of Fluids With Resonators," which was filed on May 13, 1998, by the same inventors herein. This Continuation-In-Part is being filed under 35 USC §120 and 37 CFR §1.53, and priority from that application is hereby claimed.

GOVERNMENT INTEREST

The invention described herein may be manufactured, used, sold, imported and licensed by or for the Government of the United States of America without the payment to us of any royalty thereon.

FIELD OF THE INVENTION

This invention relates generally to the field of measuring and testing fluids. More particularly, it relates to techniques of using crystal resonators as sensors for sensing fluid properties.

BACKGROUND OF THE INVENTION

Sensing a mass deposited onto a surface of a piezoelectric resonator is a technique that artisans in the measuring and testing field have used for decades. A conventional quartz crystal microbalance (QCM) typically includes a piezoelectric resonator capable of sensing loads less than a microgram. For small amounts of mass, a change in a resonant frequency of a piezoelectric resonator is proportional to a mass change. Thus, QCM's operate in a variety of diverse applications. For example, QCM's often operate as detectors for measuring humidity or the presence of other adsorbed gases in an atmosphere. In addition, QCM's operate as sensors for monitoring film thickness in thin-film deposition processes.

In the past, fabricators generally designed QCM sensors to operate in air or other gaseous environments. More recently, QCM sensors operate in liquids. The following article describes a specific application of an acoustic sensor having a quartz crystal resonator that operates in oil: Hammond et al., "AN ACOUSTIC AUTOMOTIVE ENGINE OIL QUALITY SENSOR," Proceedings of the 1997 IEEE International Frequency Control Symposium, IEEE Catalog No. 97CH36016, pp. 72–80, 28–30, May 1997.

The Hammond et al. article notes that the viscosity of oil in an automobile engine is perhaps the single most important technical parameter of a modern crankcase lubricant. Thus, Hammond et al. propose an onboard sensor for measuring viscosity changes of crankcase oil in an automobile or other similar mechanism. They describe a technique of measuring the viscosity of oil by operating an AT-cut quartz resonator immersed in the oil. The sensor includes a drive circuit that excites a shear mechanical motion in the resonator, which motion transfers to the oil as a shear wave. The oil essentially acts as a mechanical load to the quartz resonator and this mechanical load affects the quality factor Q and other electrical properties of the resonator. The Hammond et al. article describes how a change in the electromechanical quality factor Q of a resonator is proportional to the mass accumulation at the resonator-oil interface. In addition, the article explains that changes in the resonant frequency and the amplitude of a resonance signal due to the mechanical loading are each proportional to the square-root of a product of the density and viscosity of a liquid. Thus, Hammond et al. measure the combined effects of phase and amplitude changes of a sensing signal to monitor changes in an oil viscosity.

Others have used similar techniques to measure the properties of a variety of different liquids. The following articles describe resonator sensors capable of making simultaneous measurements of liquid density and viscosity: Zhang et al., "CONTRIBUTIONS OF AMPLITUDE MEASUREMENT IN QCM SENSORS," IEEE Transactions on Ultrasonics, Ferroelectrics, and Frequency Control, Vol. 43, No. 5, pp. 942–947, September 1996; and Martin et al., "MEASURING LIQUID PROPERTIES WITH SMOOTH- AND TEXTURED-SURFACE RESONATORS," 1993 IEEE International Frequency Control Symposium, IEEE Catalog No. 93CH3244-1, pp. 603–608, June 1993.

The Zhang et al. article describes how a QCM, having an AT-cut quartz resonator, detects changes in viscosity and density of a liquid. This article indicates that when a QCM operates in a liquid, the total frequency change consists of two effects, one due to mass loading and the other due to "liquid damping." Further, according to Zhang et al., one cannot distinguish a mass loading effect from a total frequency change by only frequency measurement. Thus, a standard technique of using a QCM in liquids is to simultaneously measure changes in a frequency and a quality factor Q (or changes in equivalent circuit parameters). This allows separation of mass loading effects from liquid damping effects.

The Martin et al. article describes an improved method that uses a dual-resonator sensor with two AT-cut quartz resonators, one with a smooth surface and the other with a textured or rough surface. The surface texture comprises ridges oriented perpendicular to the direction of a surface shear displacement, i.e., the X crystalline direction. When operated in a liquid, the smooth resonator generates plane-parallel laminar flow in an adjacent liquid, which causes a resonator frequency shift that is a function of liquid density and viscosity. A textured resonator, however, traps a quantity of liquid in excess of that entrained by a smooth surface. The trapped liquid behaves as an ideal mass layer, causing an additional frequency shift that depends only on density and not viscosity.

In the Martin et al. sensor, each resonator is driven by an independent oscillator circuit that provides the following two outputs: a radio frequency (RF) signal that tracks resonant frequency and a direct current (DC) voltage proportional to motional resistance. Baseline responses are determined by measuring resonant frequency and motional resistance for each resonator before its immersion in a liquid. Changes in resonator responses are then measured separately for the smooth and textured resonators after immersion. A computer connected to the sensor calculates density and viscosity. In particular, the liquid density is first calculated from the difference in responses measured between the smooth and textured devices. Having determined liquid density, the response of the smooth resonator is then used to calculate liquid viscosity. Thus, the Martin et al. method measures a frequency change and a change in quality factor Q (or a change in equivalent circuit parameters) for each resonator separately.

Although standard techniques of sensing the properties of fluids have served the purpose, they have not proved entirely satisfactory when making highly sensitive measurements of fluid properties, including viscosity and density. Sensor designers acknowledge that while changes in frequency are usually measured with great accuracy, changes in quality factor Q, motional resistance or any other quantities are measured with significantly less accuracy. Q measurements for high-Q devices are typically made with an accuracy of two to four significant figures, whereas the frequencies of stable frequency sources can be measured with an accuracy of 14 significant figures. For low-Q devices, such as resonators immersed in a fluid, the accuracy of the Q and frequency measurements is lower; however, the accuracy of the frequency measurements is still orders of magnitude higher than the accuracy of the Q measurements.

Sensor fabricators have also recognized problems with using resonators with smooth and textured surfaces. Changes in frequency and Q depend not only on a liquid's properties, but also on a resonator's surface roughness. However, it is difficult to produce surfaces of identical surface roughness, i.e., it is difficult to produce a "standard" rough surface.

An additional difficulty with the prior art is that temperature can greatly affect the properties of fluids, such as a fluid's viscosity. It is well known that, for example, the viscosity of many oils and lubricants vary with temperature and degradations due to chemical changes. Measuring frequency and Q changes alone cannot determine the temperature of a fluid simultaneously with the fluid's viscosity and density. Therefore, when only frequency and Q are measured, and a viscosity change is detected, it is not possible to determine the cause of the viscosity change. The change could be due to a temperature change or to a change in the quality of the fluid, or to a combination of such factors.

SUMMARY OF THE INVENTION

The general purpose of this invention is to provide techniques for sensing the properties of fluids primarily by means of frequency measurements. To attain this, the present invention contemplates fluid sensors that employ one or more resonators driven at a multiplicity of modes. The properties of a liquid contacting these resonators are determined by measuring a multiplicity of frequency changes, which essentially resolve various causes of these frequency changes, such as mass loading, liquid density, liquid viscosity and temperature. In addition, the present techniques involve the use of resonators that employ easily reproducible crystals, as for example polished crystals, or lapped and etched crystals. The crystals can be manufactured at low cost because the tolerances on the crystals' angles of cut and frequencies are very loose. The absolute resonant frequencies of the resonators are unimportant since the sensor system derives information from measured changes in these resonant frequencies.

According to one aspect of the invention, a sensor for determining the properties of a fluid includes one or more resonators having a liquid-contacting surface. An oscillator circuit drives each of the resonators at one or more different modes. A frequency counter connected to the oscillator monitors the operating frequencies of the resonators before and after the surfaces are placed in contact with the fluid. A computer, which is responsive to the outputs of the frequency counter, includes a liquid property system for determining difference frequencies by comparing the operating frequencies measured by the frequency counter with predetermined reference frequencies. The computer calculates the properties of the liquid from the difference frequencies.

Another aspect of the invention includes a method of determining the properties of a liquid having the following steps: establishing a reference frequency response for an acoustic resonator assembly; driving the acoustic resonator assembly in the liquid to generate acoustic waves in said the liquid out of the presence of reflected acoustic waves; measuring a test frequency response for the acoustic resonator assembly while being driven in the the liquid; measuring a shifted frequency response between the reference frequency response and the test frequency response; establishing an acoustic velocity for the liquid; and calculating the properties of the liquid using the shifted frequency response and the acoustic velocity.

The exact nature of this invention, as well as other objects and advantages thereof, will be readily apparent from consideration of the following specification relating to the annexed drawings.

DETAILED DESCRIPTION OF THE PREFERRED EMBODIMENTS

Figure 1:
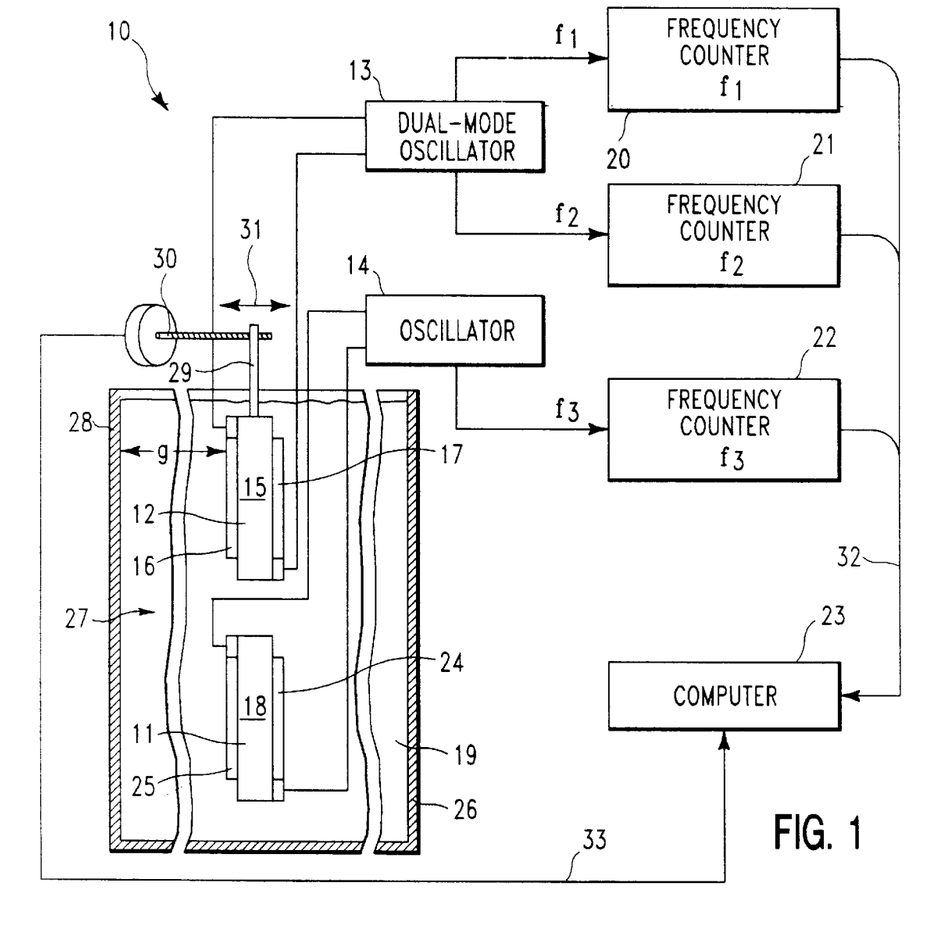
FIG. 1 is a schematic diagram, with parts in section, of a sensor system with a resonator assembly immersed in a liquid in accordance with the present invention.

Referring now to the drawings, FIG. 1 shows sensor system 10 having a crystal resonator assembly 27 immersed in non-conductive liquid 19 located in container 26. Crystal resonator assembly 27 comprises crystal resonators 11 and 12. Sensor system 10 may employ a variety of different conventional resonator types, for example, see FIGS. 2A, 2B, 10A, 10B, 11A, 11B, 12A, 12B and 13, which are described below in detail. In particular, resonator 11 represents a plano-plano singly rotated piezoelectric resonator and resonator 12 represents a doubly rotated piezoelectric resonator. Dual-mode oscillator 13 drives doubly rotated resonator 12 simultaneously at two independent modes having nominal frequencies $f_1$ and $f_2$. Oscillator 14 drives singly rotated resonator 11 at a single mode having nominal frequency $f_3$. Oscillator 13 provides two outputs; output $f_1$ connects to frequency counter 20 and output $f_2$ connects to frequency counter 21. Output $f_3$, of oscillator 14, connects to frequency counter 22. The outputs of frequency counters 20, 21 and 22 connect to computer 23 via bus 32.

Oscillator circuits capable of driving resonators 11 and 12 are well known in the art. For instance, U.S. Pat. No. 5,416,448, which issued on May 16, 1995 to Otto Wessendorf, discloses oscillator circuits of the type that may function as dual-mode oscillator 13. The Wessendorf patent describes a Lever oscillator designed for use in high-resistance resonator applications. Thus, a Lever oscillator would be particularly effective for driving resonator 12 when operating in high-viscosity mediums represented here by liquid 19. Other conventional instruments, such as network analyzers or reflectometers, can function as drivers for resonators 11 and 12.

Figure 2A:
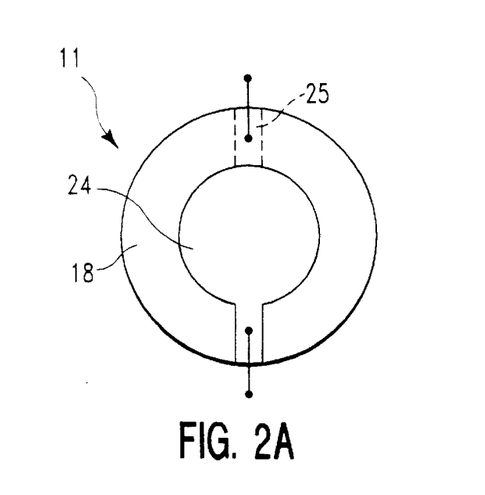
FIGS. 2A and 2B show front views of piezoelectric resonators shown in side elevations in FIG. 1.
Figure 2B:
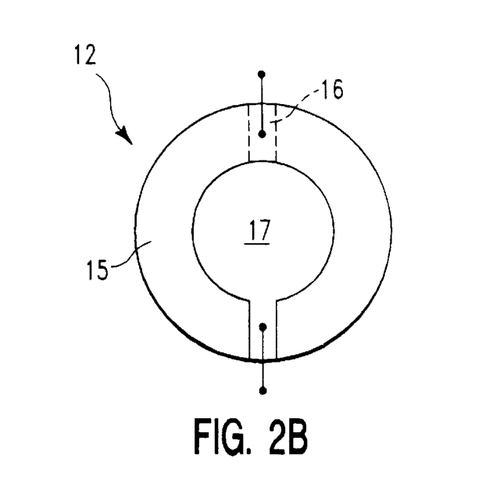

Resonator 12 includes piezoelectric plate 15 with thin-film metallic electrodes 16 and 17 deposited on opposite major surfaces thereof (see FIGS. 1, 2B, 6 and 7). Likewise, resonator 11 includes piezoelectric plate 18 with thin-film metallic electrodes 24 and 25 deposited on opposite major surfaces thereof (see FIGS. 1, 2A, 4 and 5). FIG. 2A illustrates a circular profile of the major surfaces of resonator 11. Electrodes 24 and 25 have circular portions concentrically positioned on the major surfaces of plate 18. Corresponding elements of resonator 12 have similar shapes as illustrated in FIG. 2B.

FIG. 1 further shows moveable arm 29 of high-precision motor 30 for positioning resonator 12 at selective distances from a planar, reflective side wall 28 of container 26 to form a gap having a first gap width (g). Motor 30 communicates with computer 23 via bus 33. Under the control of computer 23, motor 30 moves resonator 11 horizontally (see arrow 31) to vary the first gap width (g). During such movement, arm 29 maintains the major surfaces of resonator 11 in substantially parallel relationship with planar side wall 28.

A variety of commercial devices is available to implement motor 30. Conventional piezoelectric motors capable of achieving nanometer-scale steps over hundreds of millimeters would be effective candidates for use in sensor system 10. Acceptable implementations of motor 30 include piezoelectric bimorph and various types of commercial transducers having distance-measuring lasers, which are known to those skilled in these arts.

Figure 3:
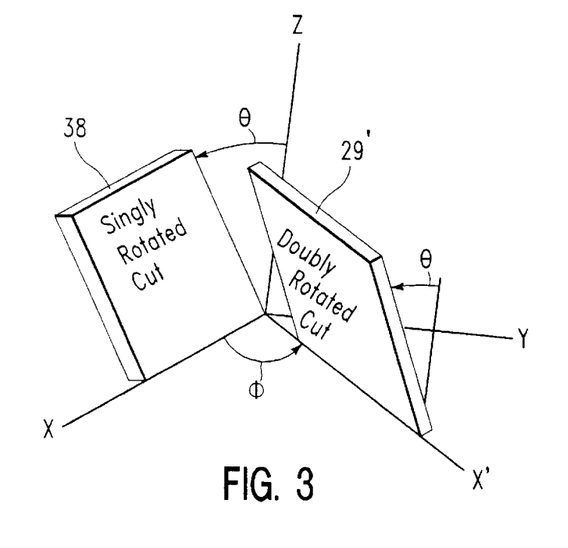
FIG. 3 is a schematic pictorial view showing slicing planes for singly rotated and doubly rotated cuts with respect to conventional orthogonal crystallographic X-Y-Z axes, and rotation angles $\theta$ and $\phi$.

Using conventional techniques, manufacturers may slice plates 15 and 18 from a piezoelectric crystal such as quartz. In this regard, FIG. 3 shows a set of conventional X-Y-Z crystallographic axes with slicing planes 38 and 29' located thereon. Plane 38 represents a plane in which a fabricator would make a singly rotated cut with respect to a crystal's X-Y-Z axes. A fabricator would make a doubly rotated cut along plane 29'. The plane of a singly rotated cut includes the X-axis while the Z-axis forms angle $\theta$ with respect to that plane. The plane of a doubly rotated cut also forms angle $\theta$ with respect to the Z-axis. In addition, the plane of a doubly rotated cut includes axis X', which lies in the X-Y plane and forms angle $\phi$ with the X-axis. A specific example of a temperature-compensated, singly rotated resonator frequently used in sensor circuits is an AT-cut quartz resonator where angle $\theta$ substantially equals 35° 15'. In this regard, Martin et al., Hammond et al. and Zhang et al., cited above, describe sensors that comprise AT-cut quartz resonators.

Doubly rotated resonators are also well known in these arts. A specific example of a temperature-compensated, doubly rotated resonator is an FC-cut quartz resonator, wherein angle $\theta$ is about 34.5° and angle $\phi$ is about 15°. Another example of a temperature-compensated, doubly rotated resonator is an RT-cut quartz resonator, wherein angle $\theta$ equals about −34.5° and angle $\phi$ is about 15°. U.S. Pat. No. 2,212,139 entitled "PIEZOELECTRIC QUARTZ ELEMENT," which issued on Aug. 20, 1940 to C. F. Baldwin, et al., discloses a multiplicity of doubly rotated quartz resonators. In addition, U.S. Pat. No. 2,743,144, entitled "ZERO TEMPERATURE COEFFICIENT PIEZOELECTRIC CRYSTAL," which issued on Apr. 24, 1956 to V. E. Bottom, et al., discloses a crystal with a doubly rotated cut, called an IT-cut, for which angle $\theta$ is about 34° 17' and angle $\phi$ is about 19.6°. Other resonator materials and/or cutting configurations will be apparent to those skilled in these arts.

Figure 4:
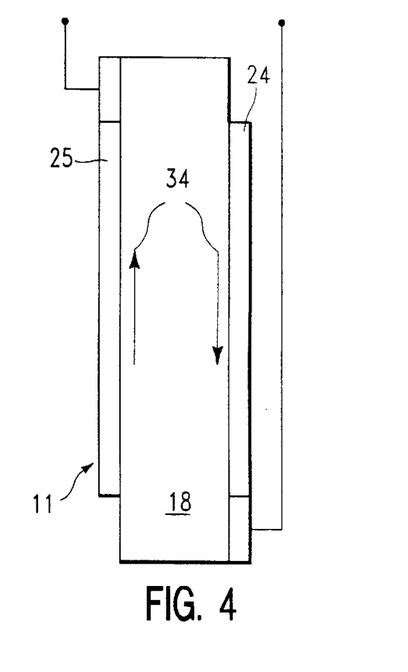
FIGS. 4 and 5 are side elevations, showing an edge of the singly rotated resonator illustrated in FIGS. 1 and 2A.

With the application of an appropriate drive voltage across electrodes 24 and 25, resonator 11 will sustain mechanical shear vibrations. Arrows 34 in FIG. 4 depict the directions of these mechanical shear vibrations at a single instant of time and represent operation of resonator 11 at a fundamental, thickness-shear mode (TSM), that is, a fundamental c-mode. Thus, displacements at the major surfaces of resonator 11 are primarily in the plane of plate 18 (small, insignificant out-of-plane components may also appear due to the finite size of the active volume of a resonator).

Figure 5:
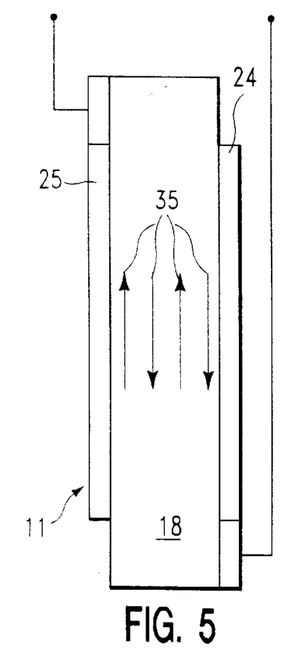

Resonator 11 may support other modes of vibration. For example, arrows 35 in FIG. 5 illustrate instantaneous vibration directions for resonator 11 when driven at a third-overtone c-mode. As indicated with arrows 34 and 35, vibrations at the major surfaces of resonator 11 are primarily directed parallel to the planar, major surfaces of resonator 11. Thus, when resonator 11 operates in liquid 19, as shown in FIG. 1, c-mode thickness shear vibrations at its surface entrain adjacent liquid layers, which results in the generation of a non-propagating, viscously coupled shear wave in liquid 19.

Figure 8:
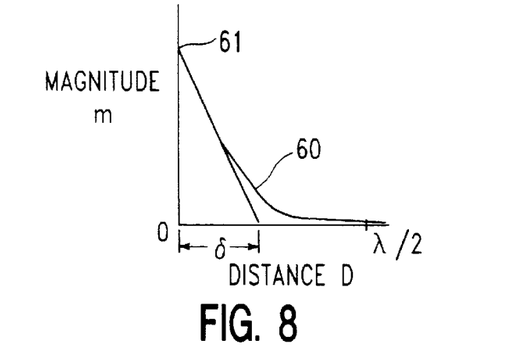
FIG. 8 is a graph of shear-wave magnitude (M) versus distance (D) useful in understanding the property of shear-wave penetration depth ($\delta$) of a liquid with an acoustic wavelength $\lambda$.

The shear-wave penetration depth ($\delta$) of a liquid is a measure of the ability of a liquid to support a shear wave. Specifically, shear-wave penetration depth ($\delta$) is related to a liquid's properties according to the following expression: $\delta = (\eta/\pi f \rho)$, where ($\eta$) is the viscosity and ($\rho$) is the density of the liquid, and f is the shear-wave frequency. Curve 60 in FIG. 8 graphically depicts shear-wave penetration depth ($\delta$) for a typical liquid. Curve 60 plots magnitude (M) of a shear wave as a function of a distance (D) measured from the shear wave source, i.e., from the face of the resonator generating the shear wave. Curve 60 shows a monotonic decrease in magnitude (M) with increasing distance (D). Shear-wave penetration depth ($\delta$) for curve 60 corresponds to that distance (D) at which the magnitude (M) is reduced to (1/e), or approximately 36.8%, of the value at the resonator surface (i.e., the maximum value depicted by point 61 in FIG. 8).

Singly rotated resonators may be driven at still other standard modes, such as a second shear mode, called the b-mode, but driving modes other than the c-mode (the slow shear mode) requires an electroding arrangement different from that of FIGS. 2A and 2B; specifically, it requires the lateral-field electrode arrangements shown in FIGS.

10A–13. In a b-mode, displacements at the major surfaces of a singly rotated resonator are primarily in the plane of the major surfaces, as in the c-mode. However, in a b-mode, surface displacements are directed perpendicular to those in a c-mode, i.e., they are directed perpendicular to arrows 34 and 35 in FIGS. 4 and 5 and parallel to the plane of plate 18. Thus, b-mode shear vibrations also result in the generation of a non-propagating, viscously coupled shear wave in liquid 19.

Yet another possible mode of vibration of a singly rotated resonator is a longitudinal mode, called an a-mode. In an a-mode, surface displacements are primarily directed perpendicular to the major surfaces. Thus, operating a singly rotated resonator in an a-mode while immersed in liquid 19 would produce propagating compression waves (also called longitudinal waves).

As indicated above, a c-mode for a singly rotated, temperature-compensated crystal, such as a plano-plano AT-cut crystal, is a pure TSM, characterized by surface displacements in the plane of the crystal plate only. On the other hand, modal displacements of doubly rotated crystals, e.g., when $\theta \equiv 35°$, and $0° > \phi \geq 30°$, are oblique, having additional components that are out of the plane of a crystal plate (see FIGS. 6 and 7). In addition, on a temperature-compensated locus of cuts, for example, as angle $\phi$ increases, the out-of-plane displacements for a c-mode of vibration also increase. The out-of-plane displacements for a b-mode and an a-mode of vibration would also change with angle $\phi$.

Figure 6:
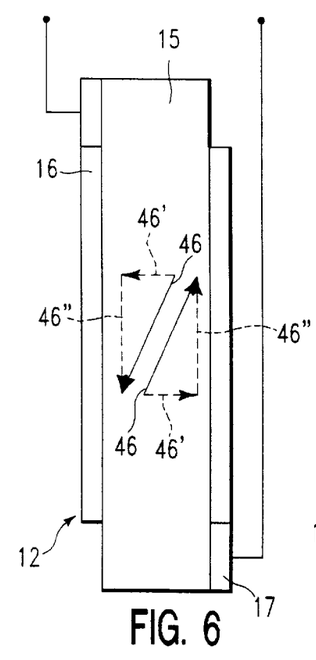
FIGS. 6 and 7 are side elevations, similar to FIGS. 4 and 5, respectively, showing an edge of the doubly rotated resonator illustrated in FIGS. 1 and 2B.
Figure 7:
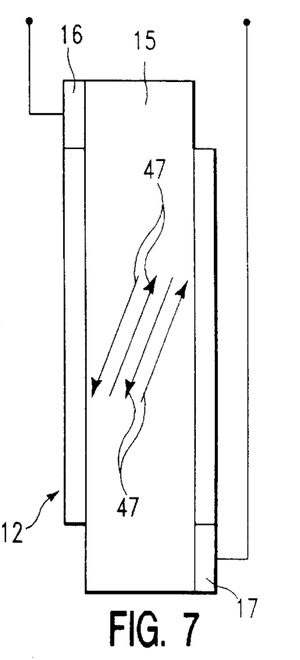

FIGS. 6 and 7 show an edge of doubly rotated resonator 12 sustaining different modes of vibration. In preparing resonator 12, a fabricator would typically slice piezoelectric plate 15 from a bulk crystal (not shown) along plane 39 (see FIG. 3) and deposit thin-film metallic electrodes 16 and 17 on opposite major surfaces thereof. Resonator 12 may represent, for example, either a standard plano-plano circular, IT-cut, FC-cut or RT-cut quartz resonator. Oblique arrows 46 in FIG. 6 depict the directions of mechanical vibration at a single instant of time that plate 15 exhibits in response to the application of an appropriate drive voltage across electrodes 16 and 17. Displacements at the major surfaces of plate 15 occur at the angle schematically indicated by oblique arrows 46.

In particular, arrows 46 may represent the displacements obtained when resonator 12 is excited on a slow, quasi-shear mode, commonly referred to as a c-mode. In addition, drive voltages may simultaneously excite resonator 12 on a fast, quasi-shear mode, called a b-mode, and/or on a quasi-longitudinal mode, called an a-mode. Moreover, doubly rotated resonator 12 can also be excited at various overtones of a given type of mode, e.g., on the fundamental, third overtone and fifth overtone.

Arrows 47 in FIG. 7 illustrate instantaneous mechanical displacements for a third-overtone c-mode of doubly rotated resonator 12. As indicated with arrows 47, the mechanical vibrations at a third overtone also occur at an angle to the major surfaces of plate 15. All told, when considering the three different modes (a-, b-, and c-modes) and the three resonant frequencies (fundamental, third overtone and fifth overtone), in principle, fabricators can build doubly rotated resonators that may be excited at one or more of nine different resonances. While seventh and higher overtones can also be excited, these modes usually exhibit high impedance, making oscillator circuit design more difficult. In addition, since the high overtones rarely provide offsetting benefits, they are rarely used.

The oblique displacements are resolvable into in-plane and out-of-plane components. For instance, FIG. 6 shows arrows 46 resolved into in-plane components 46" and out-of-plane components 46'. Arrows 47 may be resolved into similar components. Thus, when resonator 12 operates in liquid 19 (see FIG. 1), components 46' and 46" simultaneously generate shear and compression waves in liquid 19. Specifically, the displacements of in-plane components 46" generate non-propagating shear waves in a narrow liquid layer adjacent resonator 12 to a depth characterized by shear-wave penetration depth ($\delta$).

On the other hand, the displacements associated with out-of-plane components 46' generate compression waves that can propagate well into liquid 19. Liquid 19, having measurable damping characteristics, will absorb these compression waves as they propagate therein. In general, damped compression waves normally propagate away from resonator 12 toward the walls of container 26 where they may reflect if they have not yet been fully absorbed by liquid 19. Thus, depending on the location of resonator assembly 27 in container 26, reflected compression waves returning from a reflective surface, such as the walls of container 26, might impinge on resonators 11 and/or 12.

The present liquid-sensing technique involves operating resonator assembly 27 in and out of liquid 19 while computer 23 records frequency-response data via frequency counters 20, 21 and 22. Singly rotated resonator 11 may be an AT-cut quartz resonator driven at a fundamental c-mode while doubly rotated resonator 12 may be a $\phi=3°$ quartz resonator (see table A, below) driven at a c-mode fundamental and an a-mode fundamental (requires lateral excitation) or a c-mode third overtone. From the recorded frequency-response data, computer 23 calculates specific properties of liquid 19, such as density ($\rho$), viscosity ($\eta$), acoustic velocity (V), temperature (T) and shear-wave penetration depth ($\delta$).

Figure 9:
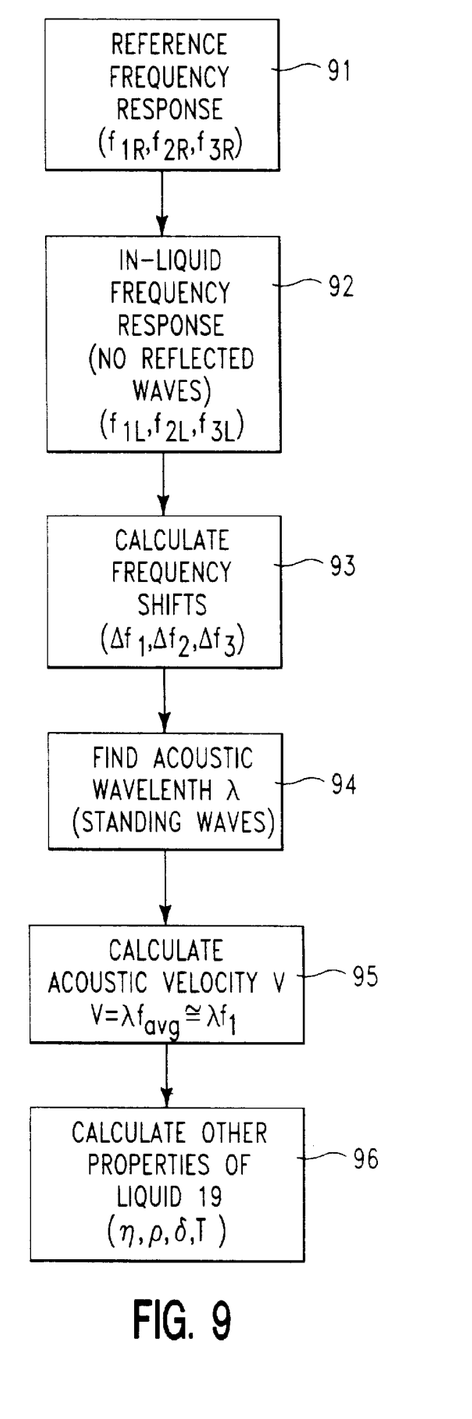
FIG. 9 is a high-level schematic diagram illustrating the operation of the sensor system of FIG. 1 in accordance with the present invention.
Figure 10A:
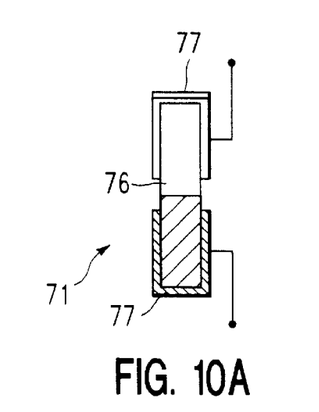
FIG. 10A is a side elevation of a resonator shown partly in a cross section taken on the line 10A—10A of FIG. 10B.
Figure 10B:
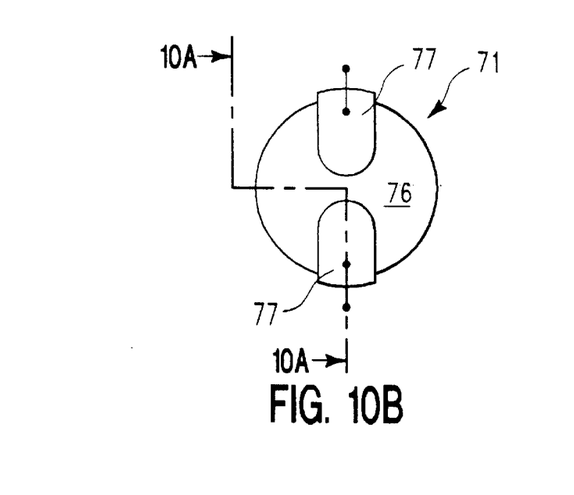
FIG. 10B is a front elevation of the resonator shown in FIG. 10A.

FIG. 9 illustrates the major steps that sensor system 10 executes when performing the present liquid-sensing technique. In STEP 91, computer 23 establishes a reference frequency response by operating resonator assembly 27 in an "unloaded" state. To achieve this, a user locates resonator assembly 27 in an ambient fluid having only negligible damping, such as air, or in a vacuum. Oscillators 13 and 14 then drive the unloaded resonators 11 and 12 while computer 23 monitors and stores their frequency responses. Specifically, oscillator 13 drives doubly rotated resonator 12 at two independent modes, causing it to resonate at frequencies $f_{1R}$ and $f_{2R}$ simultaneously. In addition, oscillator 14 drives singly rotated resonator 11 at a single mode, causing it to resonate at frequency $f_{3R}$. In STEP 91, computer 23 records the values of frequencies $f_{1R}$, $f_{2R}$ and $f_{3R}$ as being the reference (unloaded) frequencies for resonators 11 and 12. Alternatively, computer 23 can cause oscillators 13 and 14 to operate at reference points governed by switching known impedances in series or in parallel with resonators 11 and 12. By means of a calibrated set of such impedances, a table of frequencies is obtained along an "impedance circle" of each mode, instead of the single point, for example, frequency $f_{2R}$. In this scenario, the triplet of values $f_{1R}$, $f_{2R}$ and $f_{3R}$ is replaced with three series of frequencies $f_{1R_q}$, $f_{2R_q}$ and $f_{3R_q}$, where q=1, 2, 3, . . . . These frequency tables reside in the computer memory for subsequent signal processing.

Computer 23 next operates resonator assembly 27 while immersed in an ambient fluid having measurable damping characteristics and unknown properties, such as liquid 19. The mechanical loading associated with liquid 19 will generally cause the resonant frequencies of resonators 11 and 12 to deviate from their unloaded reference values ($f_{1R}$, $f_{2R}$ and $f_{3R}$) After sensor system 10 measures these frequency deviations, computer 23 calculates unknown properties of liquid 19. Unlike the prior art, the present technique will not require that sensor system 10 make measurements of changes in quality factor Q or other circuit parameters.

More specifically, oscillators 13 and 14 drive resonators 11 and 12 while immersed at various locations in liquid 19. In STEP 92, computer 23 operates resonators 11 and 12 while located at positions (typically near the center of container 26) where substantially no reflected waves will impinge thereon, all such waves having been absorbed by liquid 19. Computer 23 next records corresponding in-liquid resonant frequencies $f_{1L}$ and $f_{2L}$ for resonator 12 via frequency counters 20 and 21, respectively. In addition, computer 23 records an in-liquid resonant frequency $f_{3L}$ for resonator 11 via frequency counter 22. In STEP 93, computer 23 calculates corresponding frequency shifts as follows: $\Delta f_1=(f_{1R}-f_{1L})$; $\Delta f_2=(f_{2R}-f_{2L})$; and $\Delta f_3=(f_{3R}-f_{3L})$.

Alternatively, as noted before in the unloaded case, switching known impedances in series or parallel with resonators 11 and 12 generates a table of frequencies $f_{1Lq}$, $f_{2Lq}$ and $f_{3Lq}$ along the "loaded impedance circle" of each mode, and, mutatis mutandis, yields calculable frequency shifts as follows: $\Delta f_{1q}=(f_{1Rq}-f_{1Lq})$, etc., for subsequent signal processing.

As explained above, frequency shift $\Delta f_3=(f_{3R}-f_{3L})$ for resonator 11, which generates a shear wave in liquid 19, is a function of $(\rho\eta)^{1/2}$, where $\rho$ is the density and $\eta$ is the viscosity of the liquid. In addition, frequency shift $\Delta f_1=(f_{1R}-f_{1L})$ for resonator 12, which generates shear and compression waves in liquid 19, is a function of both $(\rho V)$, where V is the acoustic compressional velocity of liquid 19 and $(\rho\eta)^{1/2}$. Thus, by simply operating resonator assembly 27 in air and then in liquid 19, sensor system 10 is capable of measuring frequency response data related to the properties of liquid 19 in a calculable manner.

In order for computer 23 to calculate density ($\rho$) for liquid 19, sensor system 10 must first find acoustic velocity V for liquid 19, which will equal the velocity of a propagating compression wave in liquid 19. Although acoustic velocity V changes with liquid characteristics, such as temperature T, rough estimated values of acoustic velocity V for a variety of common liquids may be stored in computer 23 for later use when calculating density ($\rho$). These estimated values can be obtained from published tables and in many cases will give sufficiently accurate results. More precise values of acoustic velocity V for liquid 19 may be obtained using prior art techniques, such as those cited above (see, for example, the Hammond et al. patent). It is contemplated in the present case that computer 23 calculate, in STEP 94, acoustic velocity V by measuring acoustic wavelength $\lambda$ for liquid 19. To achieve this, computer 23 causes motor 30 to gradually move resonator 12 toward wall 28, which functions as a compression wave reflector, and into the presence of reflected compression waves. Reflected compression waves impinging on resonator 12 will represent an additional mechanical load, which sensor system 10 detects by measuring corresponding changes in the frequency response of resonator 12.

Those skilled in these arts will recognize that sensor system 10 may provide other structures for reflecting compression waves in place of wall 28. For example, sensor system 10 could include a separate reflecting panel that is not a part of container 26 to reflect compression waves toward resonator 12. In this regard, the reflecting panel may be moveable while resonator 12 may be stationary. Also, moveable arm 29 would be fixed to the moveable panel so that the motor 30 could selectively vary the first gap width (g) between the panel and the resonator 12. Sensor system 10' in FIG. 13, which is described below in detail, shows another structural arrangement for reflecting compressional waves.

As motor 30 moves resonator 12 toward wall 28, standing waves develop for certain gap widths, say gap widths ($g_1$), ($g_2$) and ($g_3$), etc. These standing waves are the result of constructive interference between the two oppositely propagating compression waves, viz., the primary compression wave generated by resonator 12 and its reflected wave from wall 28. These standing waves represent additional mechanical loading of resonator 12. The positions of resonator 12 at which a standing wave occurs, i.e. at gap widths ($g_1$), ($g_2$), ($g_3$), etc., represent multiples of one-half of an acoustic wavelength $\lambda$ from wall 28.

The loading caused by impinging reflected waves will generally become greater as motor 30 moves resonator 12 closer to wall 28 due to the reduced degree of damping. Moreover, as that loading increases it also oscillates between local maximum and minimum values due to the periodic creation of standing waves. These local maximum values will occur when resonator 12 is located at those points where standing waves take place, i.e., when the gap has gap widths ($g_1$), ($g_2$), ($g_3$), etc. Thus, the local maximums will be spaced substantially at multiples of one-half the acoustic wavelength $\lambda$.

Likewise, corresponding deviations in the resonant frequency of resonator 12 will also have local maximums spaced at multiples of one-half the acoustic wavelength $\lambda$. Hence, in STEP 94, computer 23 finds the acoustic wavelength $\lambda$ for liquid 19 by locating those points where local maximums in resonant frequency take place, i.e., finding gap widths ($g_1$), ($g_2$), ($g_3$), etc. Computer 23 then calculates the acoustic wavelength $\lambda$ for liquid 19 as being equal to twice the gap spacing, for example, $\lambda=2(g_1-g_2)$. Finally, in STEP 95, computer 23 calculates the acoustic velocity V of liquid 19 by multiplying the just-acquired acoustic wavelength $\lambda$ by an average of the resonant frequencies measured at the corresponding positions of resonator 12 as follows:

$$V=\lambda f_{avg}=\lambda[f(g_1)+f(g_2)]/2,$$

where $f_{avg}$ is an average frequency, and $f(g_1)$ and $f(g_2)$ are the resonant frequencies of resonator 12 when positioned at gap widths ($g_1$) and ($g_2$), respectively. For most practical applications, nominal frequency $f_1$ of resonator 12 may be used in place of average frequency $f_{avg}$ when calculating acoustic velocity, i.e., acoustic velocity V may be approximated from the expression $V=\lambda f_1$.

Having found acoustic velocity V, sensor system 10, in STEP 96, computes the other properties of liquid 19. Computer 23 calculates density ($\rho$) from the just-calculated value of acoustic velocity V using the known relationship involving $\Delta f_1$ and compressional velocity V. Computer 23 also calculates viscosity ($\eta$), using the just-calculated value of density ($\rho$) and the known relationship involving $\Delta f_1$ and density ($\rho$). Knowing the values of density ($\rho$) and viscosity ($\eta$) allows computer 23 to then calculate shear-wave penetration depth ($\delta$) from the relationship: $\delta=(\eta/\pi f_1\rho)$, where $f_1$ is the nominal frequency of resonator 12. Finally, the dual mode excitation of resonator 12 provides output frequency shifts $\Delta f_1$ and $\Delta f_2$ from which computer 23 calculates the temperature T of liquid 19 by making use of the known frequency-temperature characteristics of the two modes of resonator 12.

Thus, by using the technique illustrated in FIG. 9, with a calibrated means of monitoring the first gap width (g), sensor system 10 is capable of finding at least five properties of liquid 19, namely, density (ρ), viscosity (η), acoustic velocity (V), temperature (T) and shear-wave penetration depth (δ), through measurements of frequency and without the need to measure quality factor Q, as in the prior art.

The present invention contemplates numerous modifications of the above technique. For example, sensor system 10 may measure shear-wave penetration depth (δ) using an alternate technique that is independent of the calculations described above with respect to STEP 96. In this regard, in STEP 96 computer 23 calculates shear-wave penetration depth (δ) from the expression $\delta=(\eta/\pi f_1 \rho)$, where (η) is the viscosity and (ρ) is the density of liquid 19, and $f_1$ is the nominal frequency. An alternate technique of measuring shear-wave penetration depth (δ) involves moving resonator 12 into close proximity with side wall 26. These movements are such that gap width (g) ranges between zero (where resonator 12 would touch wall 26) and one-half wavelength i.e., $0<g<(\lambda/2)$. Within this close range, wall 26 encounters shear waves generated by resonator 12 (see FIG. 8 and in-plane components 46' in FIG. 6). Coupling between these shear waves and wall 26 represents still an additional mechanical load on resonator 12, which increases as gap width (g) approaches zero (see distance D in FIG. 8). The shear-wave loading Df resonator 12 manifests itself in corresponding variations in the frequency response of resonator 12. As such, frequency deviations at the output of frequency counter 20 will generally vary in a manner similar to the variations of shear-wave magnitude M in curve 60 of FIG. 8. After, storing a set of appropriate frequency changes, computer 23 determines shear-wave penetration depth (δ) by calculating, e.g., the first gap width (g) at which the frequency deviation is reduced to (1/e), or about 36.8% of its maximum value (attained for gap widths approaching zero).

Thus, this alternate technique allows sensor system 10 to measure shear-wave penetration depth (δ) directly from a succession of frequency measurements that are independent of the parameters used for the calculations performed in STEP 96. Sensor system 10 may use the results of these two independently obtained measurements of shear-wave penetration depth (δ) in a self-consistency check on the related measurements of density (ρ), viscosity (η) and acoustic velocity (V).

The present invent on contemplates other modifications of the techniques described above. For example, computer 23 may determine the unknown properties of liquid 19 by using only a single resonator, such as doubly rotated, dual-mode resonator 12. In this regard, computer 23 would make all necessary frequency measurements and calculations using only the outputs of frequency counters 20 and 21. This embodiment would employ the switching of impedances within the oscillators, described above, to generate unloaded and loaded "impedance circle" data, from which the values of density (ρ), viscosity (η) and acoustic velocity (V), etc. may be extracted by the computer in an algebraic fashion.

The invention further contemplates the use of resonators with configurations different from those of resonators 11 and 12. Resonators 11 and 12, which represent thickness-field resonators, may be replaced with lateral-field resonators, such as resonator 71 in FIGS. 10A and 10B, and resonator 72 in FIGS. 11A and 11B. Lateral-field resonators 71 and/or 72 may be singly rotated or doubly rotated resonators.

Figure 11A:
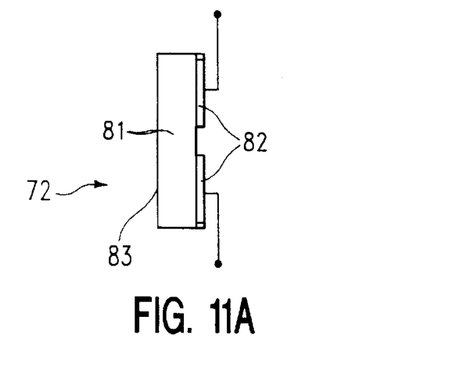
FIGS. 11A and 11B are side and front elevations, respectively, of a resonator in accordance with the present invention.
Figure 11B:
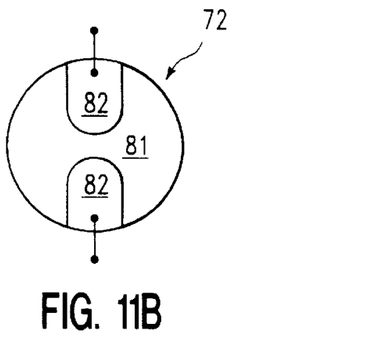

Resonator 71 comprises circular plate 76 having spaced, U-shaped electrodes 77 each deposited on both major surfaces of plate 76. When excited with an appropriate drive voltage, resonator 71 vibrates under the influence of a lateral electric field directed substantially parallel to the plane of the major surfaces of plate 76. Lateral-field resonator 72 in FIGS. 11A and 11B depicts another acceptable resonator configuration. Resonator 72 comprises circular plate 81 having spaced electrodes 82 deposited on only one of the major surfaces of plate 81, thereby leaving major surface 83 free. An appropriate drive voltage applied across electrodes 83 would produce a lateral electric field directed substantially parallel to the plane of the major surfaces of plate 81.

There are a number of situations when lateral-field resonators are preferred over thickness-field resonators. In general, thickness-field resonators are usually more expensive to manufacture than lateral-field resonators. Among the reasons advanced for the use of lateral-field resonators are the following: lessened frequency sensitivity to thermal transients; reduced aging, since the electrode is absent from the region of greatest vibrational motion; higher Q values, since electrode damping is reduced; ability to eliminate undesired modes, e.g., the b mode in SC-cut quartz; and increased stability at a given harmonic, since motional inductances are larger than with transverse-field resonators.

When both major surfaces of a resonator, e.g., resonators 11, 12, 71 and/or 72, are fully immersed, the liquid must be non-conductive to prevent the electrodes from being short-circuited by liquid 19. Those skilled in these arts, however, will appreciate that full immersion is not mandatory and that the properties of a conductive liquid may be measured by contacting only a portion of a resonator with the liquid. Methods of placing a resonator in contact with a fluid can include the following: 1) complete immersion of all surfaces (see FIG. 1); 2) partial immersion of one or both major surfaces (see FIG. 13); and 3) placing only one major surface in contact with a fluid (see FIG. 13).

Figure 12A:
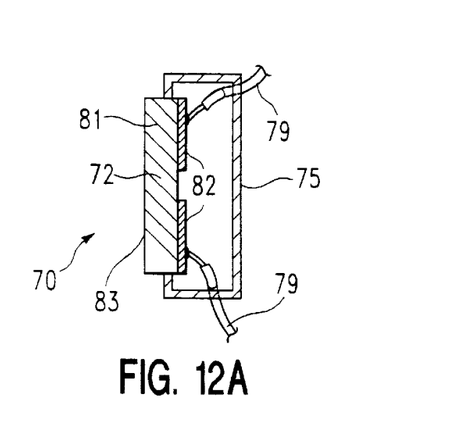
FIG. 12A is a side elevation of a resonator in cross section taken on the line 12A—12A of FIG. 12B.
Figure 12B:
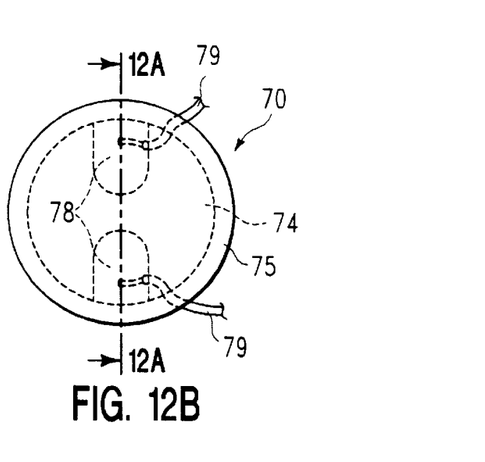
FIG. 12B is a front elevation of the resonator shown in FIG. 12A.

FIGS. 12A and 12B show sealed resonator 70, which is a modification of resonator 72 (see FIGS. 11A and 11B). Sealed resonator 70 includes cover 75, which hermetically seals electrodes 82. Cover 75 functions to prevent fluids being sensed from contacting electrodes 82. This sealing feature allows one to fully immerse resonator 70 in conductive and/or corrosive fluids without fear of shorting or damaging electrodes 82. In addition, cover 75 helps prevent mechanical damage from occurring to electrodes 82 and their delicate connections to exterior conductive leads 79.

Figure 13:
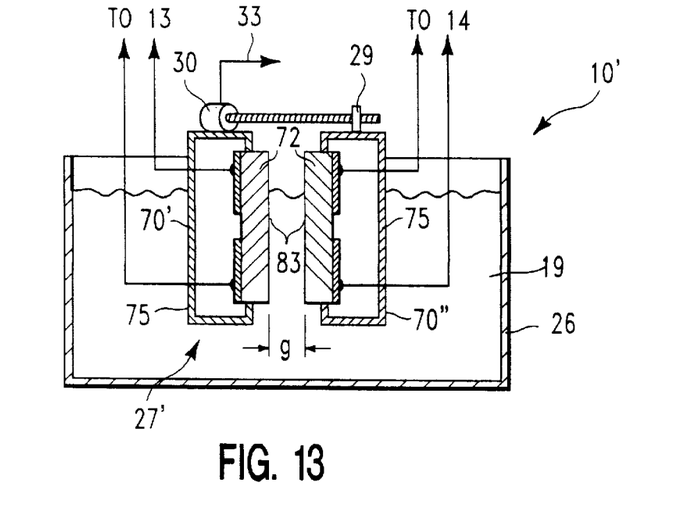
FIG. 13 is a schematic diagram with parts in section, similar to the diagram in FIG. 1, showing a portion of a modified sensor system having a plurality of piezoelectric resonators partly immersed in a liquid in accordance with the present invention.

FIG. 13 illustrates modified sensor system 10', which comprises sealed resonators 70' and 70" partially immersed in liquid 19 with their exposed major surfaces 83 facing each other and forming a second gap having second gap width, g'. Second gap width, g', can be varied via motor 30, which mounts on cover 75 of resonator 70' while moveable arm 29 is fixed to cover 75 of resonator 70". The opreation of sensor system 10' is similar to that of sensor system 10. In this regard, resonator 70' is a doubly rotated resonator, which corresponds to resonator 12 in sensor system 10, and resonator 70" is a singly rotated resonator, which corresponds to resonator 11. Thus, surface 83 of singly rotated resonator 70" generates non-propagating shear waves in liquid 19. Surface 83 of doubly rotated resonator 70" generates non-propagating shear waves and propagating compression waves in liquid 19.

While the operation of sensor system 10' is similar to that of sensor system 10, there are a few differences. In sensor system 10', the major surface 83 of singly rotated resonator 70" functions as a reflector of propagating compression waves during measurements of acoustic wavelength λ. While, sensor system 10 may operate resonators 11 and 12 simultaneously, it is preferred that sensor system 10' operate resonators 70' and 70" alternately to prevent the operation of one resonator from interfering with that of the other. Sensor system 10' includes a self-contained resonator assembly 27'. As such, sensor system 10' can find application in a variety of situations where the size, reflective nature and/or other characteristics of container 26 are not important.

A partial-immersion method, like that shown in FIG. 13, can be especially useful for resonators with angles of cut that produce large out-of-plane components of the displacement (see out-of-plane components 46' in FIG. 6). Due to the damping caused by a fluid, the frequencies of those resonators are often difficult to measure when fully immersed in a fluid. However, by immersing a resonator at a controlled rate and, therefore, gradually increasing the damping, computer 23 may also use measurements of frequency changes versus immersion depth to determine the properties of fluid 25.

In this regard, the ratios of in-plane displacements to out-of-plane displacements for particular crystal cuts and vibration modes can vary widely. The following table lists analytically derived ratio values for quartz crystals:

TABLE A

| Nazme of cut | θ (in degrees) | φ (in degrees) | Ratio of in-plane to out-of-plane displacements | | |
|---|---|---|---|---|---|
| | | | a-mode | b-mode | c-mode |
| AT-cut | 35.25 | 0 | 0.06 | 16.0 | ∞ |
| 3° V-cut | 35.07 | 3.0 | 0.07 | 15.5 | 30.4 |
| 5° V-cut | 34.94 | 5.0 | 0.09 | 15.1 | 18.2 |
| 10° V-cut | 34.6 | 10 | 0.13 | 14.2 | 9.1 |
| FC-cut | 34.3 | 15 | 0.18 | 13.4 | 6.1 |
| IT-cut | 34.1 | 19.1 | 0.22 | 13.2 | 4.8 |
| SC-cut | 33.9 | 21.9 | 0.26 | 13.6 | 4.1 |
| 25° V-cut | 33.7 | 25 | 0.29 | 14.9 | 3.6 |
| 30° V-cut | 33.4 | 30 | 0.34 | 25.5 | 3.0 |
| 42.5° V-cut | 35.8 | 42.5 | 0.42 | 4.9 | 2.9 |
| BT-cut | −49.2 | 0 | 0.21 | ∞ | 4.7 |

Another important parameter in selecting proper values for angles θ and φ for a particular sensing application is the coupling factor. Not all displacements can be realized with conventional resonators. For example, an AT-cut's a-mode and b-mode cannot be excited via thickness excitation because the coupling to these modes is zero. However, since the coupling to the c-mode is 8.8%, the c-mode can be readily excited. At φ angles greater than zero degrees, all three modes can be excited. For example, when the φ angle is equal to about five degrees, the coupling to the a-mode is 0.8%, the coupling to the b-mode is 1.3%, and the coupling to the c-mode is 8.6%.

While the present invention represents a substantial improvement of standard fluid measuring and testing techniques, important new applications of the present techniques will also appear to those skilled in these arts. For instance, due to the inaccuracies of Q measurements, prior liquid sensors typically measure relatively large changes in the properties of fluids, such as crankcase oil (see the Hammond et al. article cited above). However, because of the increased accuracy and sensitivity of the present techniques, sensors made in accordance with the present invention have important new applications, for instance, as monitors of minute irregularities in body fluids.

Obviously still other applications, modifications and variations of the present invention are possible in the light of the above teachings. While, the present techniques do not require resonators with rough or textured surfaces, the resonators employed here may have one or more of their surfaces textured. However, since it is usually easier to fabricate resonators having only easily reproducible polished surfaces, that technique is preferred.

The invention may also be applied to resonators made of materials other than quartz; for example, the langasite family of materials, and lithium tetraborate materials. In general, resonator materials are categorized, for the properties pertinent to the present invention, by the crystallographic point group. Thus, quartz and members of the langasite family belong to point group 32. Other applicable materials and their point groups include: lithium tetraborate (4 mm); certain binary piezoelectric semiconductors, such as gallium nitride, aluminum nitride, and (α-silicon carbide belonging to the wurtzite structure (6 mm); electroceramics, such as poled barium titanate and lead zirconate alloys (6 mm); and binary and ternary piezoelectric semiconductors of the zincblende structure, such as gallium arsenide and β-silicon carbide (4-bar 3 m). Plate resonators fabricated from any crystalline material will exhibit the presence of three thickness modes (the a-, b-, and c-modes previously described), and their overtones. Depending on the point group of the crystal, a singly rotated cut may have a c-mode that has its displacement in the plane of the plate; this is the case with quartz, and all materials with point symmetry 32. With materials of other symmetries, the situation may be different, but, mutatis mutandis, the teachings given herein may be applied to produce resonators whose modal frequencies are differently affected by liquid loading, and, when used in concert in the manner described herein, can be used to uniquely determine the properties of a liquid measurand.

The excitation mechanism need not be piezoelectric. Any resonator capable of being stimulated into resonant mechanical motion may be used. The means of excitation may be piezoelectricity, electrostriction, biased electrostriction (which behaves like piezoelectricity, but the coefficient can be adjusted by a dc bias), piezomagnetism, magnetostriction, biased magnetostriction, or other driving mechanism, singly, or in combination. Q change measurements may also be used in the present invention in combination with the multiple frequency change measurements In particular, the combination of the dual-resonator method of Martin et al. with the multiple-frequency-change method of the present invention can provide for simultaneous determination of density (ρ), viscosity (η), acoustic velocity (V) and temperature (T), without the movement of any resonator. Thus, many applications and variations of the present invention will become evident to those skilled in these arts in the light of the above teachings. It is understood, therefore, that within the scope of the appended claims, the invention may be practiced otherwise than as specifically described.

What is claimed is:

1. A sensor for determining the properties of a liquid, comprising:

a resonator means, having at least one liquid-contacting surface, for generating a plurality of acoustic waves in said liquid when immersed therein;

an oscillator means connected to said resonator means for driving said resonator means simultaneously at a plurality of different frequencies;

a frequency means connected to said oscillator means for measuring the operating frequencies of said resonator means when said at least one liquid-contacting surface is in contact with said liquid;

a liquid property means responsive to said frequency means for determining difference frequencies by comparing said operating frequencies measured by said frequency means with predetermined reference frequencies, and for determining said properties of said liquid from said difference frequencies;

a means for velocity for denoting an acoustic velocity for said plurality of acoustic waves in said liquid, wherein said liquid property means includes a means for determining said properties of said liquid from said acoustic velocity denoted by said velocity means and said difference frequencies;

said velocity means includes a means for measuring said acoustic velocity for said plurality of acoustic waves when propagating in said liquid;

said measuring means includes a means for measuring the wavelength of said plurality of acoustic waves in said liquid and for denoting said acoustic velocity as the product of said wavelength and the average frequency of said plurality of acoustic waves;

said resonator means comprises at least one resonator and said oscillator means drives said at least one resonator at two or more different frequencies;

said measuring means includes a reflector means for forming a plurality of gaps of different widths between said reflector means and said liquid-contacting surface of said at least one resonator, for reflecting said plurality of acoustic waves to form standing acoustic waves in said gaps at particular gap widths, and for determining the acoustic wavelength of said standing acoustic waves;

said liquid property means includes a means for calculating said acoustic velocity of said liquid from said acoustic wavelength and the frequency of said plurality of acoustic waves;

said resonator means includes a means for generating compression and shear acoustic waves in said liquid, said reflecting means includes a means for reducing said gap widths such that said acoustic shear waves extend across said gaps, and said liquid property means includes a means for determining the shear wave penetration depth of said liquid;

said properties of the liquid include determining density, $\rho$, viscosity, $\eta$, acoustic compressional velocity, V, and shear-wave penetration depth, $\delta$, through a plurality of frequency measurements without measuring quality factor, Q; and said shear-wave penetration depth, $\delta$, being related to said properties of the liquid according to the formula:

$$\delta = \eta/\pi f \rho$$

where said $\eta$ is viscosity of said liquid, said f is a shear-wave frequency and said $\rho$ is density of said liquid.

2. The sensor of claim 1, further comprising:

a pair of sealed resonators partially immersed in said liquid, each of said resonators having an exposed major surface opposing each other, to form a second gap with a second gap width, g';

a moveable arm from a motor is fixed to a cover of one of said resonators to permit varying said second gap width, g'; and employing partial-immersion for resonators with angles of cut producing large out-of-plane components of the displacement due to damping caused by said liquid causing difficulty in measuring the frequencies of said resonators when fully immersed.

3. The sensor of claim 2, further comprising one of said sealed resonators being a doubly rotated piezoelectric resonator.

4. The sensor of claim 3, further comprising one of said sealed resonators being a singly rotated piezoelectric resonator.

5. The sensor of claim 4, further comprising the exposed surface of the doubly rotated resonator generating a plurality of non-propagating shear waves and propagating compression waves in said liquid.

6. The sensor of claim 5, further comprising the exposed surface of the singly rotated resonator functioning as a reflector of said propagating compression waves during measurements of an acoustic wavelength $\lambda$.

7. The sensor of claim 6, further comprising operating said doubly rotated resonator and said singly rotated resonator alternately to prevent the operation of one of said resonators from interfering with operation of the other one of said resonators.

8. The sensor of claim 6, further comprising operating said doubly rotated resonator and said singly rotated resonator together.

* * * * *